(12) United States Patent
Cabrera et al.

(10) Patent No.: US 6,863,820 B2
(45) Date of Patent: Mar. 8, 2005

(54) MONOLITHIC SORBENTS WITH FIBRE-REINFORCED PLASTIC COATING

(75) Inventors: Karin Cabrera, Dreieich (DE); Alexander Kraus, Griesheim (DE); Willi Neuroth, Rossdorf (DE); Dieter Lubda, Bensheim (DE)

(73) Assignee: Merck Patent GmbH, Darmstadt (DE)

( * ) Notice: Subject to any disclaimer, the term of this patent is extended or adjusted under 35 U.S.C. 154(b) by 122 days.

(21) Appl. No.: 10/240,921
(22) PCT Filed: Mar. 13, 2001
(86) PCT No.: PCT/EP01/02775
§ 371 (c)(1),
(2), (4) Date: Oct. 7, 2002
(87) PCT Pub. No.: WO01/77660
PCT Pub. Date: Oct. 18, 2001

(65) Prior Publication Data
US 2003/0098279 A1 May 29, 2003

(30) Foreign Application Priority Data
Apr. 7, 2000 (DE) .......................................... 100 16 825

(51) Int. Cl.[7] .............................................. B01D 15/08
(52) U.S. Cl. .................... 210/635; 210/656; 210/198.2; 210/502.1
(58) Field of Search .................................. 210/635, 656, 210/659, 198.2, 502.1

(56) References Cited

U.S. PATENT DOCUMENTS

| 5,653,875 A | * | 8/1997 | Betz et al. ............... 210/198.2 |
| 2003/0098279 A1 | * | 5/2003 | Cabrera et al. ............. 210/656 |

FOREIGN PATENT DOCUMENTS

| WO | WO 94/19687 | * | 1/1994 | ............... 210/198.2 |
| WO | WO 95/03256 | * | 2/1995 | ............... 210/198.2 |
| WO | WO 98/59238 | * | 12/1998 | ............... 210/198.2 |

OTHER PUBLICATIONS

PTO Translation PTO 2000–647 of WO 94/19687 dated Dec. 1999, pp. 1–17.*

* cited by examiner

Primary Examiner—Ernest G. Therkorn
(74) Attorney, Agent, or Firm—Millen, White, Zelano & Branigan, P.C.

(57) ABSTRACT

The invention relates to monolithic sorbents with a casing of fiber-reinforced plastic. Through the use of fiber-reinforced plastic having a viscosity of between 40 and 100 ml/10 min by the MVI method, the casing can be applied to the moulding leaving just a small dead space and has adequate mechanical stability.

10 Claims, 3 Drawing Sheets

A

B

A

B

MONOLITHIC SORBENTS WITH FIBRE-REINFORCED PLASTIC COATING

REFERENCE TO RELATER APPLICATIONS

This application is a 371 of PCTIEO01/02775 filed Mar. 13, 2001.

The invention relates to monolithic sorbents which are encased with tubes of fibre-reinforced plastic. This facilitates the mechanically stable encasing of monolithic sorbents leaving just a small dead space.

For the production of conventional chromatography columns with particulate sorbents, the packing material is introduced into a stainless-steel or plastic tube with tight-fitting ends. The result of this is that the sorbent bed is in close contact with the jacket of the column, and the particles are homogeneously distributed over the entire cross section of the column.

If, as disclosed, for example, in WO 94/19687 and in WO 95/03256, particulate sorbents are replaced by monolithic sorbents, the problem arises of sealing the casing of the sorbent in a liquid-tight and pressure-stable manner. Inorganic or organic mouldings can shrink during production, and consequently may not remain in the original casing. They have to be provided with a new liquid-tight and pressure-stable casing. Only in this way is it ensured that sample and eluent are transported exclusively through the sorbent.

Various ways of encasing monolithic sorbents in a liquid-tight manner are disclosed in DE 197 26 164. These include, for example, encasing with pressure-stable plastics, such as, for example, PEEK (polyether ether ketone) or fibre-reinforced PEEK. However, attempts to encase monolithic sorbents with materials of this-type have shown that the mechanical stability of the casing is not the only crucial factor.

The quality of a monolithic column for HPLC can be described via the separation efficiency (N/m) on the one hand and via the peak symmetry on the other hand. A good analytical column has separation efficiencies of 70,000–100,000 N/m. The peak shape corresponds in the ideal case to a Gaussian bell shape. Deviations from this symmetrical shape result in "fronting" or "tailing". The inherent separation efficiency of the column body and the peak symmetry should not change any further in the chromatographic use test after encasing with a polymer for solvent-tight sealing.

In the case of unsuitable casings, the polymer is not in contact with the column body leaving just a small dead space. The column exhibits pre-peaks or at least "peak fronting" from the beginning as a consequence of faster sample transport at the column body/polymer interface.

Casings with unsuitable polymers can also give good separation efficiency and peak symmetry in the first chromatographic test, but result in a change/impairment in the two quality parameters on further use.

One phenomenon is an increase in peak tailing when the column is stored in the mobile phase (for example storage in acetonitrile/water, 60/40 for 4 weeks) as a consequence of the microporous structure of the casing. A further phenomenon may be an increase in peak fronting at the same time as a decrease in separation efficiency owing to a change in the geometry of the casing.

It has been found that these unfavourable phenomena are caused by the natural shrinkage properties of polymers on the one hand and by the swelling properties in solvents on the other hand. The encasing of rigid, brittle inorganic mouldings, for example made of silica gel, is particularly problematic. Since the polymer (for example PEEK) is melted onto the moulding at high processing temperatures, it initially adheres strongly thereto. On cooling of the polymer, "movements" (shrinkage) of the polymer occur while the moulding remains rigid in its dimension. Stresses build up in the process. If the polymer now comes into contact with solvents, it adsorbs the latter and swells. In the process, the stresses that have built up are dissipated in the longitudinal and transverse directions. As a consequence, small destruction of the porous silica-gel body occur at the interface. The inherent movement of the polymer, which adheres strongly to the silica gel, causes the formation of holes by "entrainment" of silica gel at the interface. This results in a decrease in the separation efficiency, and in the extreme case in strong peak fronting.

An increase in peak tailing can be explained by a micropore structure in the polymer casing, causing uncontrolled additional diffusion phenomena during the chromatography process.

These results show that a casing for monolithic sorbents should ideally have all of the following properties;

Solvent-stable to the conventional solvents in chromatography, such as, for example, acetonitrile, MeOH, water, dioxane, heptane, etc., since the mobile phase consists of one or more of these components.

Mechanically stable in order to be able to effect faster chromatography without problems at relatively high flow rates. At relatively high flow rates, a back-pressure builds up within the column. The polymer should not change its geometry even at a back-pressure of up to 200 bar.

In contact with the monolithic column body leaving just a small dead space in order to avoid drops in separation efficiency and fronting of the substance peaks or pre-peaks due to uncontrolled eluent streams at the polymer/column body interface.

Pore-free in order to avoid disadvantageous tailing of the substance peaks due to uncontrolled diffusion phenomena in micropores of the casing.

The object of the present invention was therefore to provide suitable casings for monolithic columns which meet the above-mentioned requirements. In particular, the object was to improve contact with the monolithic column body leaving just a small dead space.

It has been found that the viscosity of the polymers used for the casing is of particularly great importance for contact with a monolithic moulding leaving just a small dead space. The mechanical stability can be achieved, in particular, by fibre reinforcement. Only fibre-reinforced polymers in a certain viscosity range accordingly meet the requirements with respect to chemical and mechanical stability and can at the same time be applied to the monoliths leaving just a small dead space.

The present invention therefore relates to monolithic mouldings which are encased with a fibre-reinforced thermoplastic leaving just a small dead space, where the fibre-reinforced plastic has values of between 40 and 100 ml/10 min, measured by the MVI method.

In a preferred embodiment of the present invention, the fibre reinforcement is produced by carbon fibres.

In a preferred embodiment of the present invention, the thermoplastic polymer is PEEK (polyether ether ketone).

The present invention also relates to a chromatography column containing a moulding encased in accordance with the invention.

BRIEF DESCRIPTION OF THE DRAWINGS

The present invention also relates to the use of a moulding encased in accordance with the invention for the chromatographic separation of at least two substances.

DESCRIPTION OF THE PREFERRED EMBODIMENTS

Figure 1:
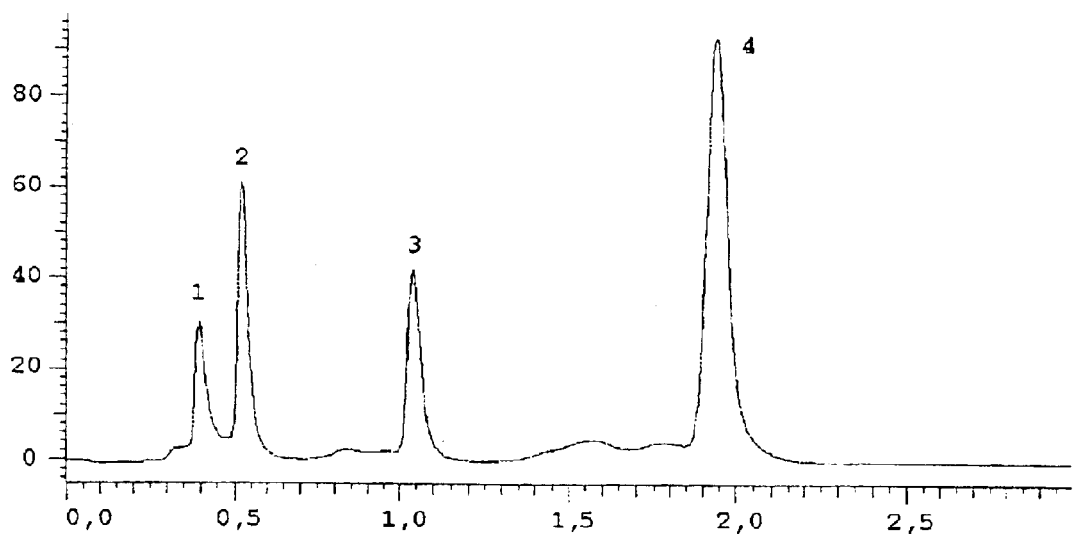
FIGS. 1 to 3 show chromatograms of separations carried out with moulding encased in various ways. Further details are given in Examples 1 to 3.
Figure 1:
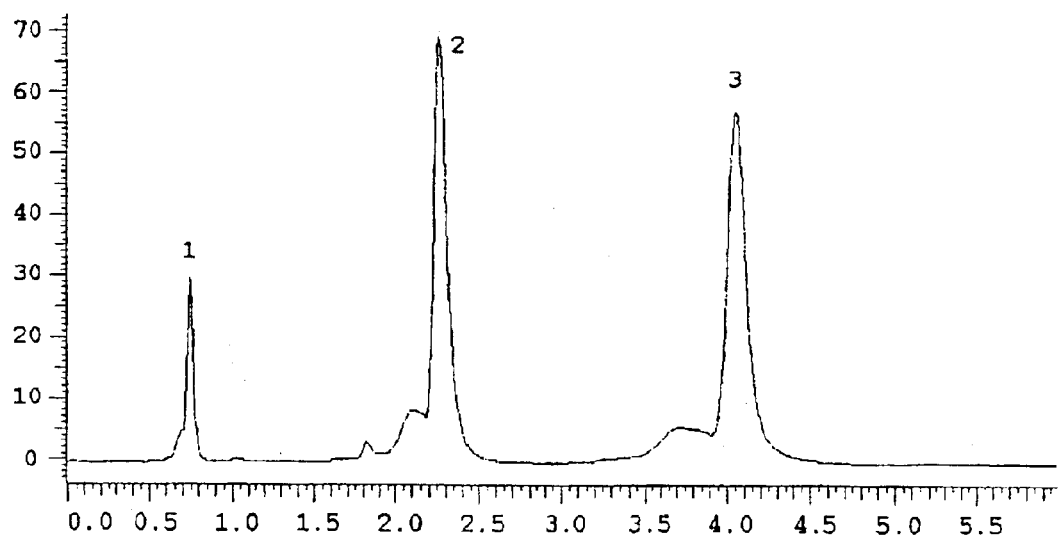

For the purposes of the present invention, encasing leaving just a small dead space means that the dead space between the monolithic moulding and the casing is so small that it exerts no adverse effect on the separation efficiency of the chromatography column.

The casing according to the invention can be used to encase organic and inorganic mouldings and inorganic/organic hybrid mouldings, as employed, for example, as sorbents for chromatography purposes. For chromatographic separations, the mouldings are usually modified with separation effectors, but this generally has no effect on their other properties. The casing according to the invention is particularly suitable for rigid, inflexible mouldings. In particular, brittle, inorganic mouldings, as disclosed in WO 94/19687, WO 95/03256 or WO 98/29350, can be encased leaving just a small dead space in accordance with the invention.

Plastics which are suitable for the casing according to the invention are thermoplastic polymers, such as, for example, polyaryls, polyether ketones, polyesters, aromatic polyamides, polyimides, polybenzimidazoles, preferably fluorinated polymers, polyphenylene sulfides, polyether sulfones or liquid-rystalline polymers (LCPs), as well as mixtures of two or more of these materials. Particular preference is given to PEEK (polyether ether ketone). In addition to different viscosities, these materials exhibit, in particular, different chemical stability, such as, for example, solvent stability. The choice of the plastic which is suitable for a casing therefore also depends on the chemical stability later required.

PEEK exhibits adequate chemical stability for most applications. The following comments are therefore based partly on PEEK as material example. However, a person skilled in the art is able to apply the following disclosure to other plastics with different viscosities, chemical stabilities, etc.

It has been found that a casing of pure plastic does not meet the requirements of mechanical and chemical stability. In particular, mouldings encased with pure plastic exhibit unsatisfactory separation efficiency. The initially good separation efficiency owing to encasing initially leaving just a small dead space drops since the polymer swells due to solvent contact and the casing detaches from the moulding (see Example 2). In addition, shrinkage phenomena occur during cooling of the plastic after application to the moulding. Furthermore, the pressure stability of some plastics is inadequate.

These disadvantages can be eliminated through the addition of stabilisers, such as fibre materials, inorganic materials or pigments, for example chalk, talc, mica or inorganic oxides, such as silicon dioxide. In accordance with the invention, particular preference is given to the use of fibre-reinforced plastics comprising fibre materials, such as, for example, glass or in particular carbon fibres as stabilisers. Besides a reduction in the natural swelling and shrinkage properties of the polymer, fibres exhibit a particularly effective increase in the mechanical stability.

The more fibres are added to the plastics as stabilisers, the more brittle the plastics become. Most plastics are therefore only sufficiently flexible to be converted into columns up to a content of 40% of fibres. The fewer fibres are added, the greater the extent to which the swelling and shrinkage properties of the polymers occur. Since it is precisely these properties that are to be reduced by the addition of fibres, the fibre content should be at least 15%. The plastics are preferably provided with a fibre content of 20–35%, particularly preferably 27–33%.

On encasing of mouldings with fibre-reinforced plastics, only a slight decrease in the separation efficiency, or none at all, was observed, even on extended storage in solvents or on frequent use.

However, not all stabiliser-reinforced plastics can be used for encasing mouldings leaving just a small dead space. In order to be applied effectively to the moulding, the moulding must have a certain viscosity.

In the plastics-processing industry, the viscosity of thermoplastics is usually determined in accordance with the melt volume index (MVI) in accordance with DIN ISO 1133. The method is carried out in a standardised apparatus. Its central constituents are a heatable, vertical cylinder (internal diameter 9.55 mm) with exit nozzle (internal diameter 2.06 mm, length 8.00 mm) and a matching piston with (apparatus-readable) position marks (30.00 mm) and which can be loaded with a weight. The apparatus contains precise measurement systems for determining the distance through which the piston has moved and for time and temperature measurement.

In order to determine the viscosity of the plastics for a column casing according to the invention, a method based on ISO 1133 was used: In order to carry out the determination, the apparatus is pre-heated to a defined temperature of 380° C. The pre-dried (150° C., 12 hours) plastic or plastic compound (6 g of powder or granules) is introduced into the cylinder and compressed. When the measurement temperature (380° C.) has been reached, the temperature is held for a further 240 seconds. The weight (10 kg) is then automatically added, and the melt is allowed to flow out. The measurements begin when the lower position mark on-the piston is recognised and end when the upper mark is recognised. The melt volume index (MVI) is then determined by the instrument software from the distance through which the piston has moved, the measurement time intervals (2 seconds) and the known piston area and output in the usual unit of ml/10 min.

The pre-drying time and temperature) (150° C., 12 hours), the sample mass (6 g), the measurement temperature (380° C.), the weight (10 kg) and the measurement time intervals (2 seconds) are standards aimed specifically at the MVI determination of PEEK and PEEK compounds. The instrument geometry and the waiting time (240 seconds) are stipulated in ISO 1133.

Plastics exhibit different viscosities, inter alia depending on their degree of crosslinking and their chain length. The addition of stabilisers, such as, for example, fibres, changes the viscosity of the substances again. They become significantly more viscous. These aspects have to be taken into account when selecting a plastic which is suitable in accordance with the invention.

Plastics are generally available as granules or powders. Both forms can be employed for the casing according to the invention. However, it must be noted that the viscosity of powders can change during subsequent processing steps, while this usually does not occur in the case of granules. The reason for this is that powders frequently originate directly from the polymerisation batch and still contain a residual content of monomers and oligomers. During compounding, the monomers escape in gas form, and post-polymerisation can occur. This can easily increase the viscosity of the plastics.

It has been found that on addition of 30% of fibres, only plastics having an initial viscosity of greater than 120 ml/10 min by the MVI method are suitable for encasing leaving just a small dead space. At values below 120, the plastics become so viscous after compounding that, although they can still be extruded to give tubes, they can only be applied to the mouldings in an unsatisfactory manner. The upper limit for the MVI values of the plastics which are suitable according to the invention is essentially determined by the availability of the plastics. For example, PEEK with more than 250 ml/10 min by the MVI method is not usually available. However, the plastics should not become too liquid on melting onto the moulding.

Preference is therefore given to pulverulent plastics having an MVI of from 150 to 210, particularly preferably between 180 and 210. In the case of granules, preference is given to materials having an MVI of from 120 to 200, particularly preferably from 150 to 170.

For the moulding casing according to the invention, the plastics are firstly compounded, i.e. they are mixed with additives, such as, for example, fibres, colorants, etc. This is preferably carried out by controlled addition of the additives with simultaneous processing via an extruder screw. More precise process parameters are known to the person skilled in the art and are given in handbooks, such as, for example, Hensen, Knappe and Potente, "Handbuch der Kunststoffextrusionstechnik" [Handbook of Plastic Extrusion Technology], Karl Hanse Verlag (1986/1989).

During compounding, the later viscosity of the plastic is influenced through the type of additives added and partly also by the time of addition. In the case of early addition of fibres, these are comminuted during compounding, for example, fibres having an initial length of 6 mm may only have an average length of a few $\mu$m after compounding. For the casing according to the invention, the length of the added fibres is of minor importance, since the subsequent processing steps also cause comminution of the fibres. Fibres are therefore usually added at an early stage.

The viscosity of the fibre-reinforced plastics which are suitable according to the invention is typically, after compounding with about 30% of fibres, between 40 and 100 ml/10 min by the MVI method, preferably between 50 and 70 ml/10 min by the MVI method, the upper limit, as already in the case of non-fibre-reinforced starting materials, being determined principally by availability.

After compounding, tubes are produced from the material mixture by known processes, such as extrusion or injection moulding. Shaping processes of this type are known and are revealed, for example, by textbooks, such as Knappe, Lampl and Heuel, "Kunststoffverarbeitung und Werkzeugbau" [Plastics Processing and Mould Construction], Karl Hanse Verlag (1992).

The monolithic moulding is subsequently introduced into the plastic tube. The tube is then brought into the closest possible contact with the moulding by warming. This step is crucial for encasing leaving just a small dead space. Only materials having the viscosity which is suitable according to the invention can be brought into sufficiently close contact with the moulding. In this step, it is advantageous to use homogeneous tubes which have a uniform wall thickness over their entire length.

Suitable processes are known to the person skilled in the art, for example from the production of insulated cables. One way of producing monolithic sorbents encased in this way consists, for example, in extruding the plastic onto the moulding. Here, the monolithic moulding is transported parallel to the extrusion of a tube through a crosshead die. The freshly extruded tube surrounds (hot) the moulding and is additionally pressed against the moulding, for example by a pressure device. It is also possible here to warm a pre-shaped tube instead of producing a tube by extrusion. This mechanical pressure and the additional sintering during cooling cause the formation of a tight casing. It is also possible to introduce the moulding into a prefabricated tube whose internal diameter is slightly larger than the external diameter of the moulding and then to warm the plastic so that the tube can be taken off at the end diameter and surrounds the moulding closely.

In a further variant, the plastic casing is produced by flame spraying or single or multiple shrinking-on.

For use as a chromatography column, the monoliths encased in accordance with the invention can then be provided with corresponding connectors, filters, seals, etc. The casing can terminate flush with the sorbent or project at the ends. Designs of this type are known for chromatography columns with particulate or monolithic sorbents.

The monolithic sorbents encased in accordance with the invention exhibit excellent separation properties. Even after storage in solvents and frequent use, only a slight impairment in the separation efficiencies, or none at all, is evident. The casing according to the invention thus ensures for the first time the production of chromatography columns which are both mechanically and chemically stable and are in contact with the monolithic mouldings leaving just a small dead space.

Even without further details, it is assumed that a person skilled in the art will be able to utilise the above description in the broadest scope. The preferred embodiments and examples should therefore merely be regarded as descriptive disclosure which is absolutely not to be regarded as limiting in any way.

The complete disclosure content of all applications, patents and publications mentioned above and below, in particular the corresponding application DE 100 16 825, filed on 07.04.2000, is incorporated into this application by way of reference.

Examples

Chromatographic separations with monoliths encased in various ways

The separation examples were carried out under the following chromatographic conditions:

Eluent: acetonitrile/water 60/40 (v/v)

Flow rate: 2 ml/min

Temperature: room temperature

Injection vol.: 10 $\mu$l

Detection: UV 254 nm

The chromatograms shown in FIGS. 1A, 2A and 2B show the separation of the following sample:

1. Thiourea
2. 2,2'-Bipyridine
3. Naphthalene
4. Anthracene

Figure 2:
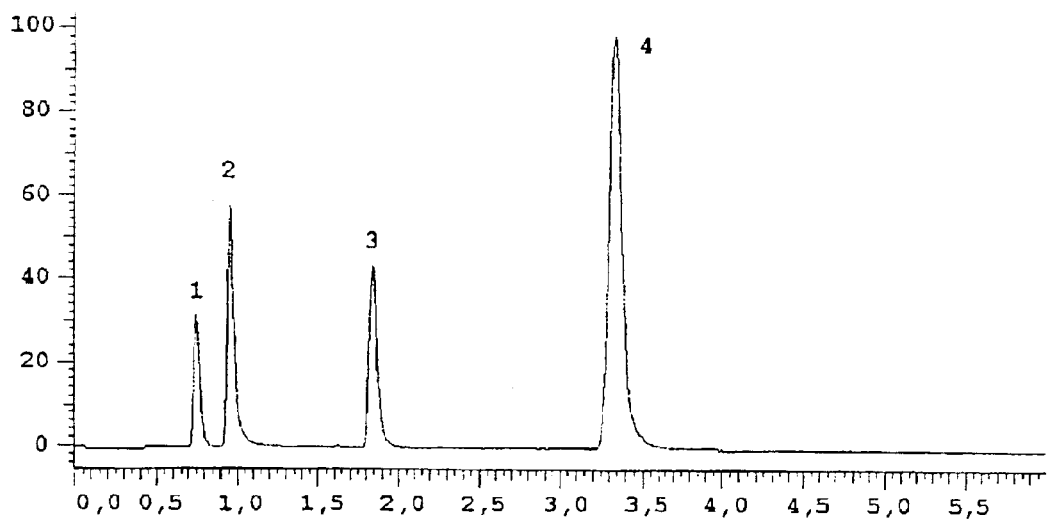
Figure 2:
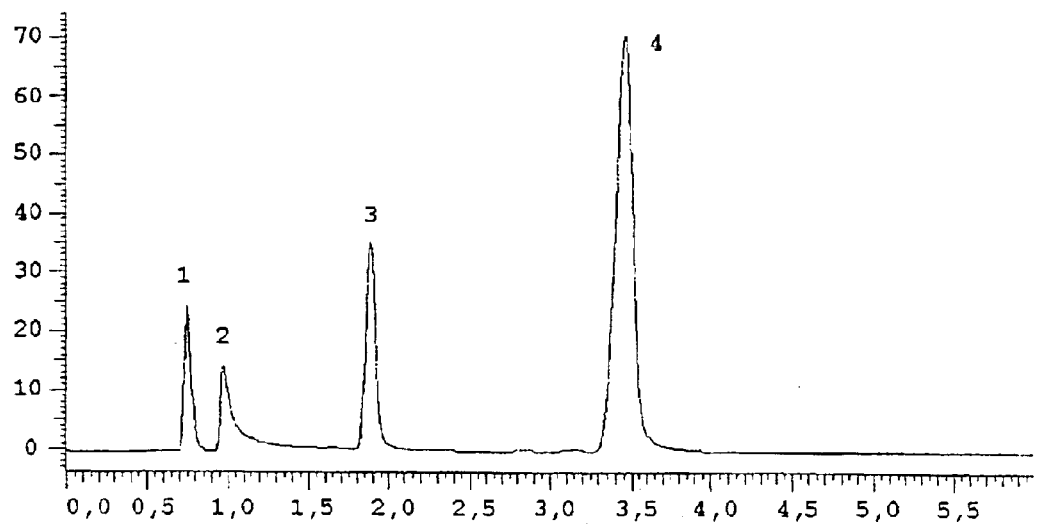
Figure 3:
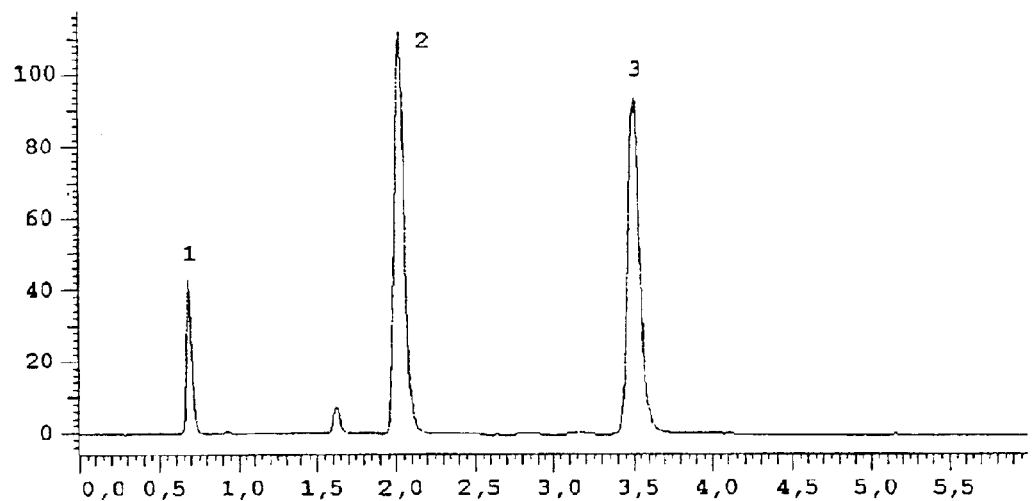
Figure 3:
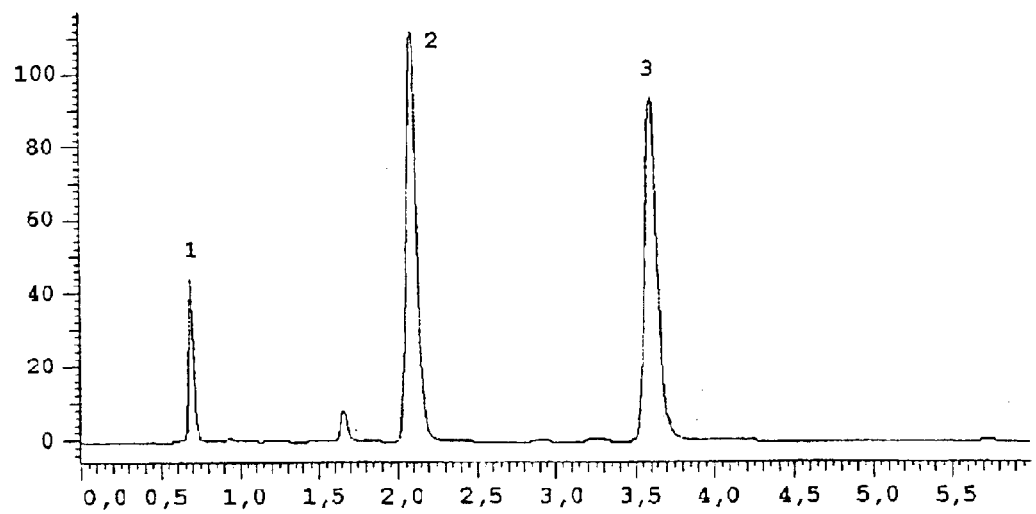

FIGS. 1B, 3A and 3B show the separation of:
1. Thiourea
2. Progesterone
3. Anthracene The numbering of the analytes in the chromatograms (FIGS. 1 to 3) corresponds to the numbering indicated above.

The retention time in minutes is indicated in each case on the abscissa of the chromatograms, and the intensity of the detector signal in mV is indicated on the ordinate.

Example 1 Encasing with an excessively viscous plastic

FIG. 1A shows the chromatogram of a separation on a column whose sorbent corresponds to that of a Chromolith® SpeedROD RP-18e, 50-4.6 mm column (produced in accordance with WO 98/29350). The chromatogram of FIG. 1B was recorded on a column whose sorbent corresponds to that of a Chromolith® Performance RP-18e, 100-4.6 mm column (produced in accordance with WO 98/29350). The viscosity of the fibre-reinforced PEEK used for the casing was 29.7 ml/10 min by the MVI method and was thus too high. The casing is thus not in contact with the sorbent leaving just a small dead space. The typical pre-peaks which are clearly evident in both chromatograms occur.

Example 2 Encasing with a non-fibre-reinforced plastic

FIGS. 2A and 2B were recorded on a column containing a sorbent corresponding to Chromolith® Performance RP-18e, 100-4.6 mm. FIG. 2A shows the first chromatogram recorded directly after the encasing. For peak 4, a separation efficiency of 96,900 N/m and an asymmetry in accordance with USP of 1.23 were obtained. FIG. 2B shows a separation recorded on the same column after storage for 3 weeks (in acetonitrile/water 60/40). For peak 4, a separation efficiency of 53,000 N/m and an asymmetry in accordance with USP of 0.96 were now obtained.

This result can be attributed to the fact that the casing consists of non-fibre-reinforced PEEK. During storage, changes in geometry causing lower separation efficiency occur due to shrinkage or swelling.

Example 3 Casing according to the invention

The chromatograms shown in FIGS. 3A and 3B were recorded on a column corresponding to Chromolith® Performance RP-18e 100-4.6 mm. The casing tube consists of PEEK with 30% of carbon fibres, MVI=70 ml/10 min.

FIG. 3A shows the first chromatographic test directly after the encasing. FIG. 3B shows the re-test after storage for 4 weeks in acetonitrile/water 60/40.

The separation efficiency of the column is equally good in both separations. For peak No. 3 (anthracene), the following values, for example, were determined:

First test: efficiency=105,000 N/m, tailing (USP)=1.19
Re-test: efficiency=110,000 N/m, tailing (USP)=1.18

What is claimed is:

1. A monolithic moulding device comprising a monolithic moulding suitable for the chromatographic separation of at least two substances which is encased with a fibre-reinforced thermoplastic leaving just a small dead space, wherein the fibre-reinforced plastic has a viscosity of 40 to 100 ml/10 min, measured by the MVI method.

2. A monolithic moulding device according to claim 1, wherein the fibre reinforcement is carbon fibres.

3. A monolithic moulding device according to claim 1, wherein the thermoplastic is polyether ether ketone.

4. A chromatography column containing a monolithic moulding according to claim 1.

5. A process of chromatographically separating at least two substances comprising separating at least two substances with the monolithic moulding of claim 1.

6. A monolithic moulding device according to claim 1, wherein the fibre-reinforced thermoplastic has a fibre content of 20–35%.

7. A monolithic moulding device according to claim 1, wherein the fibre-reinforced thermoplastic has a fibre content of 27–33%.

8. A monolithic moulding device according to claim 1, wherein the MVI method is in accord with DIN ISO 1133.

9. A monolithic moulding device according to claim 1, wherein the fibre-reinforced plastic has a viscosity of 50 to 70 ml/10 min, measured by the MVI method.

10. A monolithic moulding device according to claim 1, wherein the fibre-reinforced thermoplastic has a fibre content of about 30%.

* * * * *